United States Patent [19]

Huber

[11] 4,162,849

[45] Jul. 31, 1979

[54] SELECTED ELEMENT CONCENTRATION FOR FLAMELESS ATOMIC ABSORPTION SPECTROSCOPIC MEASUREMENTS

[75] Inventor: Bernhard W. Huber, Überlingen, Fed. Rep. of Germany

[73] Assignee: Bodenseewerk Perkin-Elmer & Co., GmbH, Überlingen, Fed. Rep. of Germany

[21] Appl. No.: 887,265

[22] Filed: Mar. 16, 1978

[30] Foreign Application Priority Data

Mar. 22, 1977 [DE] Fed. Rep. of Germany ....... 2712420
Jun. 4, 1977 [DE] Fed. Rep. of Germany ....... 2705409

[51] Int. Cl.$^2$ ............................................. G01N 1/28
[52] U.S. Cl. ...................................... 356/36; 356/312
[58] Field of Search ........................... 356/36, 85, 244

[56] References Cited

U.S. PATENT DOCUMENTS 3,957,374  5/1976  Kriese et al. ........................... 356/85

OTHER PUBLICATIONS

Woodriff, *Applied Spectroscopy*, vol. 28, No. 5, 1974, pp. 413-416.
L'vov, *Talanta*, vol. 23, 1976, pp. 109-118.
L'vov, *Spectrochimica Acta*, vol. 24B, 1969, pp. 53-70.

*Primary Examiner*—F. L. Evans
*Attorney, Agent, or Firm*—Salvatore A. Giarratana; Francis L. Masselle; Richard G. Besha

[57] ABSTRACT

The desired element in a specimen to be analyzed by atomic absorption spectroscopy is deposited in the spectroscope measuring tube in a concentrated form by first distilling away all components of the specimen that are more volatile than the element, then increasing the heat to distill off the desired element which is condensed on the cooler walls of the measuring tube while all components less volatile than the element will remain in the adjacent heated specimen crucible.

22 Claims, 3 Drawing Figures

SELECTED ELEMENT CONCENTRATION FOR FLAMELESS ATOMIC ABSORPTION SPECTROSCOPIC MEASUREMENTS

BRIEF SUMMARY OF THE INVENTION

In atomic absorption spectroscopy, an illuminating source is used which emits light having a line spectrum that contains the lines that are characteristic of the desired element to be analyzed. A specimen sample containing this desired element is injected into the spectroscope graphite measuring tube which is heated to a temperature that will vaporize the sample and break down its components into an atomic cloud within the graphite tube. The spectroscope light beam is then directed through the graphite measuring tube where its intensity is absorbed according to the quantity of the desired element in the sample and the beam output is then directed to a spectrophotometer which measures the intensity of the spectro line characteristics of the desired element in the specimen.

Because the light source of the atomic absorption spectrometer emits a line spectrum containing the spectral lines characteristic of the desired element in the sample, the measuring beam is attenuated, in principle, only by atoms which absorbed the same spectral lines, or those produced by the desired element in the sample. However, there is a certain background absorption caused by the remaining components in the sample. Certain components of the sample are capable of absorbing those spectral lines that are characteristic to the desired element. Furthermore, components in the sample that are less volatile and are not atomized by the heat applied to the graphite tube may generate smoke that produces an overall attenuation of the measuring beam passing through the graphite tube. It is apparent, therefore, that if the desired element is contained in the sample of a specimen in a very low concentration together with such other interfering components, the measurements produced by the spectrophotometer may be inaccurate and unuseable.

Briefly described, the invention is for a concentrating process in which a small sample of the specimen is placed in a crucible adjacent the bore of the graphite measuring tube, both being in a container through which an inert gas may flow. Both crucible and the graphite tube are heated to a temperature below that which will atomize the desired element so that the low temperature interfering components will be distilled from the sample and carried away by the inert gas flow. Additional heat is then applied to the crucible only to increase its temperature to the point where the desired element will distill from the remaining sample and, because the inner walls of the graphite measuring tube are at a lower temperature, the desired element will become concentrated on the cooler walls of the tube. The graphite measuring tube may then be used in the atomic absorption spectroscopic apparatus in the conventional manner.

DESCRIPTION OF THE DRAWINGS

In the drawings which illustrate preferred embodiments of the invention.

DETAILED DESCRIPTION

Figure 1:
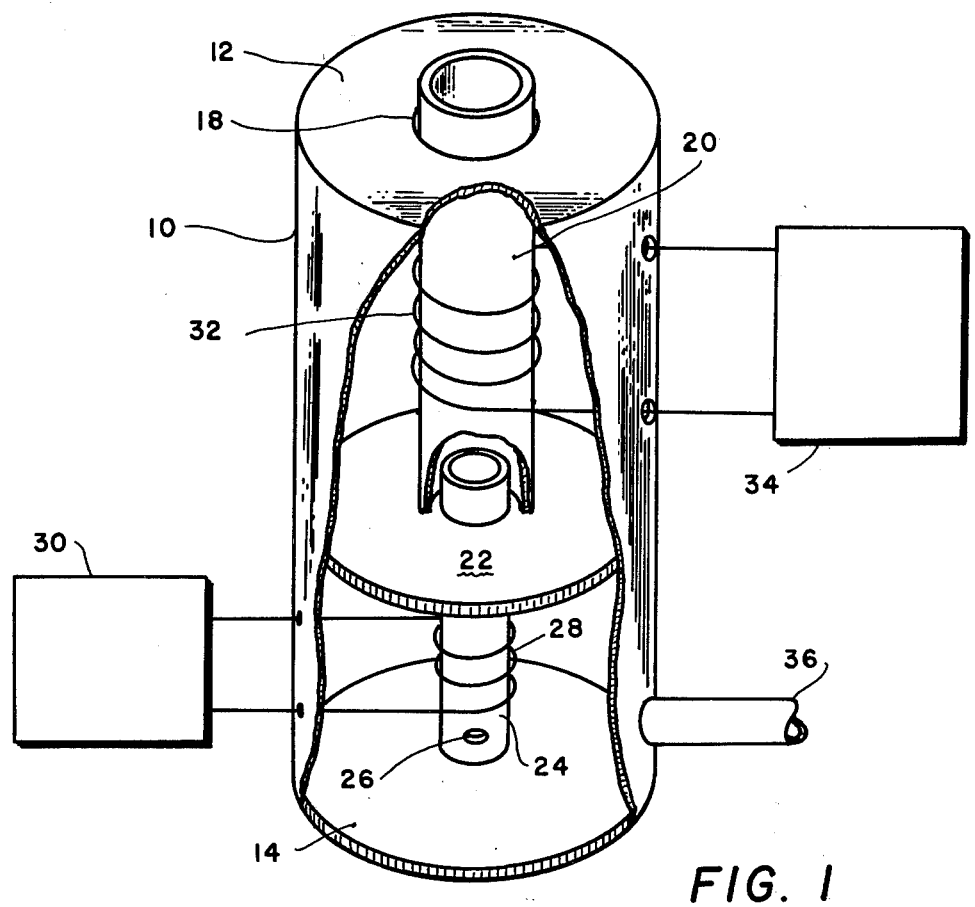
FIG. 1 is a sectional perspective view illustrating one embodiment of a device for concentrating the desired element in a specimen into the bore of a graphite measuring tube.

FIG. 1 is a sectional view of one embodiment of the apparatus in which a desired element to be analyzed may be condensed in concentrated form on the inner walls of the graphite furnace tube while eliminating most of the interfering components of the specimen that are more volatile and also less volatile than the desired element to be measured. The apparatus illustrated in FIG. 1 comprises a cylindrical housing 10 having an upper end wall 12 and a lower end wall 14. Upper end wall 12 has a central circular aperture 18 of sufficient diameter to permit adequate clearance for the admission of a graphite furnace tube 20, one end of which extends above the wall 12 and the opposite end of which rests upon a circular partition 22 within the housing 10.

Partition 22 is provided with a coaxial aperture that is smaller than the inside diameter of the graphite tube 20 but which has a diameter sufficiently large to accommodate a tubular graphite crucible 24, one end of which extends above the top surface of the partition 22 and the opposite end of which is closed but above the top surface of the bottom end wall 14. A small lateral hole 26 radially extends through the wall of the crucible 24 near its lower end. Crucible 24 is provided with suitable means for heating and atomizing a specimen placed within its bore. Preferably, such heating is accomplished by low voltage current heating through the graphite of the crucible but, for clarity, is illustrated in FIG. 1 as a heater coil 28 controlled by a suitable current source 30. Similarly, the graphite tube 20 is illustrated as being heated by a similar heating coil 32 under the control of a suitable current source 34. An inert gas inlet port 36 is provided in the cylindrical wall near the base of the housing 10.

In operation, prior to the insertion of the graphite tube 20 into aperture 18, a suitable sample quantity of the specimen is placed in the crucible 24. The graphite tube 20 is then inserted and current sources 30 and 34 are activated to heat the crucible 24 and graphite tube 20 to a temperature slightly below that at which the desired element to be measured becomes volatile. At this lower temperature, most of the more volatile interfering components in the sample will become volatile and a flow of inert gas through the inlet port 36 will enter the lateral bore 26 of the crucible 24 and carry these components through the crucible 24 and the graphite tube 20 to be exhausted in the atmosphere. Because the graphite tube 20 is maintained at the same temperature as the crucible 24, the escaping vapors of these components will not adhere to the inner walls of the tube 20.

After removal of the more volatile components of the sample, crucible 24 is further heated to the temperature at which the desired element to be measured becomes volatile. The temperature of the graphite tube 20 is not increased but is preferably maintained at the previous temperature so that the vapors of the desired element emerging from the crucible 24 will adhere to the cooler inside wall of the graphite tube 20, while any remnants of the more volatile components will not condense but will pass into the atmosphere.

Components from the sample that are less volatile than the desired element to be measured are not vaporized and remain within the crucible so that the inner wall of the graphite tube will carry a concentrated sample of the desired elements to be measured. Thereupon, the tube 20 is removed from the housing 10 and placed in a conventional graphite tube atomizer for analysis in the conventional manner by an absorption spectrometer.

Figure 2:
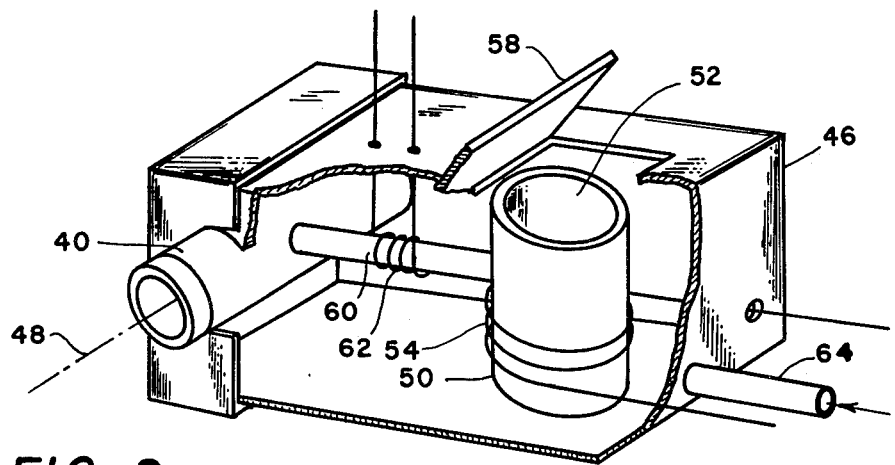
FIG. 2 is a sectional perspective view of a second embodiment of the invention in which the desired element is concentrated in the graphite measurement tube while it remains in the absorption spectroscope fixture.

FIG. 2 is a sectional view of an embodiment of apparatus that will condense the desired element within a graphite measuring tube without removal of the graphite tube from the atomic furnace of the absorption spectrometer. In this embodiment, a graphite measuring tube 40 with conventional heating end electrodes is located within a housing 46, the side walls of which are provided with suitable apertures, coaxial with the center bore of the tube 40, to permit passage of the measuring beam, indicated by the center line 48, to axially pass through the bore of the tube 40. Located within housing 46 and spaced from the tube 40 is a tubular crucible 50 having a sealed lower end and an open upper end 52 and provided with suitable means for heating, as indicated by the heating coils 54. Located in the top wall or roof of housing 46 above the upper end 52 of the crucible 50, is an opening that may be sealed with a suitable cover 58.

The bore of the crucible 50 communicates with the bore of the graphite tube 40 by a small pipe section 60 which extends between a radial opening in the walls of the crucible 50 to the radial opening in the wall of the tube 40. Pipe section 60 is also provided with a heater 62. As with the embodiment illustrated in FIG. 1, the housing 46 in FIG. 2 is provided with a gas inlet port 64.

The operation of the embodiment of FIG. 2 is similar to that of FIG. 1. Cover 58 is first removed and the specimen is inserted into the crucible 50. Subsequently, cover 58 is closed and, if desired, the crucible 50, pipe section 60, and tube 40 may be heated to a temperature of approximately 100° to first dry the sample. Admission of an inert gas through the inlet port 64 will enter the upper end 52 of the crucible 50 and will carry the vapors from the crucible through the pipe section 60 and the graphite tube 40 to be exhausted through the housing apertures that are coaxial with the tube. Subsequently, the crucible 50, pipe section 60, and graphite tube 40 may be heated to a suitable elevated temperature, for example, approximately 500° C., at which temperature some of the interfering components in the sample become volatile and are thereby carried away through the pipe section 60 and through the ends of the graphite tube 40. Subsequently, the crucible 50 and pipe section 60 are heated to a temperature at which the desired element to be measured becomes volatile. Graphite tube 40 remains at the lower temperature so that the desired element will condense upon the cooler walls of the tube while any remaining more volatile interfering components will be purged from the system. The vaporization of the desired element in the sample in the crucible 50 may be continued until a sufficient quantity of the substance has condensed on the inner wall of the graphite tube 40, whereupon the housing with crucible 50 may be removed and the graphite tube may be heated to an atomizing temperature in the conventional manner and whereby a cloud of atoms of sufficient density is formed within the tube 40 so that the measuring beam of the absorption spectrometer will produce a sufficiently large output signal. As with the embodiment of FIG. 1, interfering components that are less volatile in the desired element will remain within the crucible and will not condense in tube 40.

Figure 3:
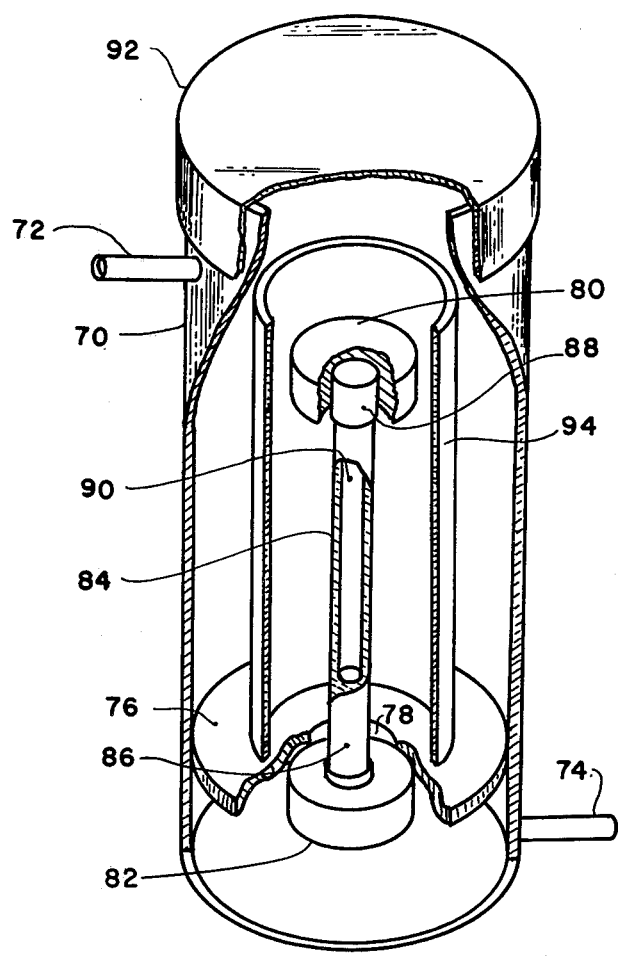
FIG. 3 is a sectional perspective view of a third embodiment of the invention in which the specimen-carrying crucible is in the form of a thin tube axially suspended in the bore of a graphite measuring tube.

FIG. 3 is a sectional elevation view of an embodiment in which the desired element will adhere to the graphite tube, more volatile components will be flushed away, and less volatile components will not distill from a crucible or cuvette that is heated to only one high temperature. This embodiment includes a tubular container 70 through which an inert gas is passed via ports 72 and 74. Container 70 is divided into an upper and lower chamber by an annular support shelf 76 having a central aperture 78. An electrode 80 in the upper chamber and a second electrode 82 in the lower chamber, their mountings not shown, support a graphite cuvette 84 which passes axially through the aperture 78 in the shelf 76. Cuvette 84 is preferably a graphite rod having a solid lower end 86, a hollow bore or cavity 90, and an open upper end that is sealed with a bore plug 88 during operation. The cavity 90 is formed within the cuvette 84 for carrying a very small sample of a specimen for analysis.

The tubular container 70 is normally sealed during operation and is provided with a removable cover 92 which is removed to enable the placement of a conventional graphite atomizing tube 94 into the apparatus. Graphite tube 94 is placed on shelf 76 and is substantially coaxial with the cuvette 84 and spaced therefrom to permit an inert gas flow between the outer wall of cuvette 84 and the inner wall of the tube 94.

In operation, a cuvette, such as the cuvette 84, is provided with a sample of the specimen to be analyzed and the bore plug 88 seals the sample within the cavity 90. Thereupon, the cuvette is inserted between the electrodes 80 and 82 of the described apparatus and the graphite measuring tube 94 is coaxially placed over the cuvette 84 and on the shelf 76. The cover 92 is replaced on the container 70 and an inert gas is permitted to flow through the inlet port 72 and from the exhaust port 74 to both cool the graphite tube 94 and also eliminate possibility of combustion within the container 70. Current is then passed through electrodes 80 and 82 and through the graphite cuvette 84 to heat the cuvette to an elevated temperature at which the desired element to be analyzed becomes atomized and diffuses through the graphite wall of the cuvette 84 to adhere to the cooler inner surface of the graphite 94. The more volatile components of the sample also diffuse through the wall of cuvette 84. However, since the graphite tube 94 is heated by radiation from the curve 84 but maintained slightly cooler by the gas flow, the graphite tube will not condense most of the more volatile components and they will be flushed from the system. All non-atomized less volatile components remaining in the cavity 90 form a smoke that will not diffuse through the graphite wall. When all components have been suitably atomized, the heating current is switched off and the graphite tube 94 may then be removed from the container 70 and mounted in the atomizer apparatus of the absorption spectrometer in the conventional manner.

What is claimed is:

1. A method for concentrating a desired element of a sample in a graphite furnace tube for atomic absorption spectroscopy, said method comprising the steps of:

heating the sample to the vaporization temperature of the desired element in a zone near the bore of the graphite tube; and maintaining said graphite tube at an elevated second temperature that is lower than said vaporization temperature whereby said desired element will condense on the inner surface of said graphite tube.

2. The method claimed in claim 1 wherein said sample is heated in a crucible in communication with the bore of said graphite tube.

3. The method claimed in claim 2 further including the step of admitting a flow of inert gas through said crucible and said graphite tube.

4. The method claimed in claim 3 further including a preliminary step of heating said crucible and said graphite tube to said second temperature whereby components in said sample that are more volatile than said desired element will be distilled from said sample and exhausted from said graphite tube by said inert gas flow.

5. The method claimed in claim 4 further including a first preliminary step of heating said crucible and said graphite tube to a third temperature lower than said second temperature, whereby the sample is first dried.

6. The method claimed in claim 3 whereby said crucible communicates with the bore of said graphite tube by a heatable tube in open communication between the bore of said crucible and the bore of said graphite tube.

7. The method claimed in claim 6 whereby said crucible, said graphite tube and said heatable tube are in an enclosed container and said graphite tube may be mounted in an atomizing furnace of an absorption spectrometer.

8. The method claimed in claim 2 wherein said crucible is an enclosed graphite cuvette mounted between electrodes and wherein said cuvette diffuses atomized components through its graphite walls and into said graphite tube.

9. The method claimed in claim 8 further including the step of admitting a flow of inert gas through said graphite tube and around said cuvette.

10. The method claimed in claim 9 wherein said graphite tube and said cuvette are coaxially positioned within a container.

11. The method claimed in claim 9 including the step of applying an electrical current flow through said electrodes and said graphite cuvette for atomizing the sample contained within said cuvette.

12. Apparatus for concentrating a selected element of a sample for atomic absorption spectroscopy comprising, in combination:

a graphite furnace tube, means for heating the sample to the vaporization temperature of the selected element in a zone near the bore of the graphite tube to generate vapors of the selected element for flow into the bore of said graphite tube;

means for maintaining said graphite tube at an elevated second temperature, lower than said vaporization temperature whereby the vapors of said selected element will condense on the inner surface of said graphite tube.

13. Apparatus according to claim 12 wherein said means for heating the sample to the vaporization temperature of the desired element includes a crucible in communication with the bore of said graphite tube.

14. Apparatus according to claim 13 further comprising means for flowing inert gas through said crucible and said graphite tube.

15. Apparatus according to claim 14 further including means for heating said crucible and said graphite tube to said second temperature whereby components in said sample that are more volatile than said selected element will be distilled from said sample and exhausted from said graphite tube by said inert gas flow.

16. Apparatus according to claim 15 further including means for heating said crucible and said graphite tube to a third temperature lower than said second temperature, whereby the sample is first dried.

17. Apparatus according to claim 14 including a heatable tube for providing open communication between said crucible and the bore of said graphite tube.

18. Apparatus according to claim 17 further comprising a container for enclosing said crucible, said graphite tube and said heatable tube.

19. Apparatus according to claim 13 wherein said crucible includes a pair of electrodes, and an enclosed graphite cuvette mounted between said electrodes whereby atomized components are diffusable through the graphite walls of said cuvette and into said graphite tube.

20. Apparatus according to claim 19 further including means for flowing inert gas through said graphite tube and around said cuvette.

21. Apparatus according to claim 20 wherein said graphite tube and said cuvette are coaxially positioned relative to one another.

22. Apparatus according to claim 20 further including means for applying an electrical current flow through said electrodes and said graphite cuvette for atomizing the sample contained within said cuvette.

* * * * *

UNITED STATES PATENT OFFICE
CERTIFICATE OF CORRECTION

Patent No. 4,162,849        Dated July 31, 1979

Inventor(s) Bernhard W. Huber

It is certified that error appears in the above-identified patent and that said Letters Patent are hereby corrected as shown below:

Title Page, Paragraph [30] Foreign Application Priority Data, line 2, numeral "2705409" should read -- 2725409--.

Column 4, line 54, change "curve" to --cuvette--.

Signed and Sealed this

Twenty-eighth Day of October 1980

[SEAL]

Attest:

SIDNEY A. DIAMOND

Attesting Officer

Commissioner of Patents and Trademarks